United States Patent [19]

Harwood

[11] 4,343,688
[45] Aug. 10, 1982

[54] METHOD OF MAKING HUMIDITY SENSORS

[75] Inventor: Mervyn G. Harwood, Bromley, England

[73] Assignee: U.S. Philips Corporation, New York, N.Y.

[21] Appl. No.: 207,485

[22] Filed: Nov. 17, 1980

[30] Foreign Application Priority Data

Nov. 22, 1979 [GB] United Kingdom ............... 7940446
Jul. 28, 1980 [GB] United Kingdom ............... 8024630

[51] Int. Cl.³ .................... G01N 27/28; G01N 27/42
[52] U.S. Cl. .......................... 204/195 W; 310/313 R; 338/35; 427/125
[58] Field of Search ............ 204/195 W, 1 W; 427/125; 338/35; 367/191; 73/52, 49.3, 73, 336; 310/313 R, 313 B, 313 C

[56] References Cited

U.S. PATENT DOCUMENTS

| | | | |
|---|---|---|---|
| 3,188,283 | 6/1965 | Cole | 204/195 W X |
| 3,337,441 | 8/1967 | Goldsmith | 204/195 W |
| 3,916,367 | 10/1975 | Nicholas et al. | 338/35 |
| 3,926,745 | 12/1975 | Czuha | 204/1 T |
| 3,954,590 | 5/1976 | Czuha | 204/195 W |
| 4,016,308 | 4/1977 | Frazee | 427/125 |
| 4,052,691 | 10/1977 | Nagano et al. | 338/35 |
| 4,272,986 | 6/1981 | Lowry | 73/73 |

FOREIGN PATENT DOCUMENTS

1018192 1/1966 United Kingdom .......... 204/195 W

OTHER PUBLICATIONS

Elias J. Amdur et al., Science & Industry, vol. 2, pp. 428–432, (1965).

Primary Examiner—G. L. Kaplan
Attorney, Agent, or Firm—Marc D. Schechter

[57] ABSTRACT

A method of making a humidity sensor which comprises an alumina substrate bearing a pair of noble metal electrodes. The electrodes are electrically connected to each other by an electrically conductive moisture-sensitive layer present on the substrate. In order to be able to monitor the moisture content of a gaseous atmosphere inside the housing of a sealed electronic device, for example an integrated circuit or an acoustic surface wave device, it is necessary to use a small sensor which can be used in a static atmosphere. According to the method, an electrode system may be formed by sputtering gold onto an alumina substrate. The substrate bearing the electrode system is then baked in air at a temperature in the range of from 100° to 750° C. for from 30 hours to ½ hour, and then a coating comprising orthophosphoric acid or phosphorus pentoxide is applied over that area of the substrate which is to bear the moisture-sensitive layer. The assembly is heated at from 50° to 500° C. for from 30 hours to ½ hour so as to form the electrically conductive, moisture-sensitive layer by a reaction between the alumina and the orthophosphoric acid or the phosphorus pentoxide.

4 Claims, 5 Drawing Figures

METHOD OF MAKING HUMIDITY SENSORS

BACKGROUND OF THE INVENTION

The invention relates to a method of making a humidity sensor. The sensor comprises an electrically insulating substrate bearing an electrode system comprising a pair of noble metal electrodes. The electrodes are electrically connected by an electrically conductive, moisture-sensitive layer present on the substrate. The invention also relates to a humidity sensor made by such a method, to a hermetically sealed electronic module containing such a humidity sensor, and to a hermetically sealed surface acoustic wave device containing such a humidity sensor. Such an electronic module may for example, be a discrete semiconductor device, an integrated circuit or a computer module.

Humidity sensors for determining the moisture content of gaseous atmospheres are well-known. These sensors comprise a substrate bearing a pair of noble metal electrodes between which a layer of a hygroscopic agent, for example phosphorus pentoxide or lithium chloride, is disposed. The hygroscopic agent absorbs the moisture from the gaseous atmosphere. When the humidity sensor is used to determine the moisture content of a flowing gaseous atmosphere, the moisture content is usually determined coulombmetrically; a direct current voltage is applied across the electrodes, the water absorbed by the hygroscopic agent being electrolyzed, a steady state is then established between the moisture content of the gas and the moisture content absorbed in the hygroscopic agent.

United Kingdom Patent Specification No. 1,018,192 describes such a humidity sensor in which the hygroscopic agent is phosphorus pentoxide. A disadvantage of such sensors is that after the hygroscopic agent has been exposed to an atmosphere having a relatively high moisture content, for example the ambient atmosphere, it takes a considerable time to establish equilibrium at a relatively low moisture content. There will, of course, be limitations on the environment in which phosphorus pentoxide can be used as the hygroscopic agent. The humidity sensors described in Specification No. 1,018,192 are intended for use in flowing gaseous atmospheres.

An article entitled "The use of Relative Humidity Sensors to Monitor the Atmosphere within Hermatically Sealed Electronic Modules" by Elias J. Amdur and Harold G. Lofgren, (in Humidity and Moisture, Measurement and Control in Science and Industry, Volume 2, Applications edited by E. J. Amdur, Reinhold 1965), pages 428–432), describes the use of humidity sensors to monitor the humidity content of the atmosphere within computer modules. The moisture-sensitive elements in these sensors were polyvinyl alcohol-lithium chloride films, and had sensitivites over the range from 3.5 to 16% relative humidity. The moisture was determined by measuring the resistance of the moisture-sensitive elements using an A.C. ohmmeter.

It is well-known in semiconductor technology that all materials adsorb and absorb oxygen, nitrogen and water from the ambient atmosphere. Hermetically sealed housings are used to isolate semiconductor devices from the ambient atmosphere in which the device is used. The device may be sealed into such a housing in an inert atmosphere, for example dry nitrogen. Some semiconductor devices are affected by oxygen, and many semiconductor devices are affected by moisture. If the device is properly sealed into a housing, there will be no ingress of moisture into the housing containing the device after sealing. But moisture will be evolved into the atmosphere inside the sealed housing as a result of desorption from the inside surfaces of the housing and the surfaces of the device if the surfaces have not been dried adequately prior to sealing the housing.

Mass spectroscopy has been used to examine the moisture contents of the atmosphere within a sealed package, but this is a technique which cannot be used for continuous moisture monitoring. This technique is not suitable for measuring low moisture contents in atmospheres of packages having small internal volumes.

SUMMARY OF THE INVENTION

An object of the invention is to provide a method of making a humidity sensor suitable for determining the moisture content of a static atmosphere and which can be used for determining the moisture content of the atmosphere inside small hermetically sealed housings having internal volumes, which are on the order of 100 cubic mm.

The invention provides a method of making a humidity sensor which comprises an alumina substrate bearing an electrode system comprising a pair of noble metal electrodes. The electrodes are electrically connected to each other by an electrically conductive, moisture-sensitive layer present on the substrate. The method comprises the steps of forming the electrode system on the alumina substrate, and then activating the exposed alumina by heating it to a temperature in the range of from 100° to 750° C. for from 30 hours to ½ hour. This heating step also serves to remove undesired residual impurities from the substrate surface. After this, a coating comprising orthophosphoric acid or phosphorus pentoxide is applied over the electrodes and over that area of the substrate which is to bear the electrically conductive, moisture-sensitive layer. Finally the substrate, electrode system and coating are heated at from 50° to 500° C. for from 30 hours to ½ hour so as to form the electrically conductive, moisture-sensitive layer by a reaction between the alumina and the orthophosphoric acid or the phosphorus pentoxide.

It will be evident to a person skilled in the art that shorter heating steps are required for heat treatments which are performed at higher temperatures than for heat treatments performed at lower temperatures. For example, the moisture-sensitive layer may be formed using a heat treatment at a temperature in the range from 200° to 300° C. for a time of from 4 hours to ¾ hour.

When the coating comprises orthophosphoric acid, it is referred to use N/2 to 27 N orthophosphoric acid. When solutions which are less than N/2 were used, it was found that the sensitivity of the moisture-sensitive layer is low.

The electrode system in the humidity sensor is generally formed by depositing a film of a noble metal onto the alumina substrate. The film is deposited from the vapor phase, and the electrode system is formed from the noble metal film by selective chemical etching. The noble metal film is preferably deposited by sputtering, since sputtered films have better adhesion to alumina substrates than do evaporated films. The electrode system may also be produced by screen printing a suitable conductive paste, and then firing at a sufficiently high temperature to produce good adhesion of the electrode system to the substrate.

During the investigations which led to the invention, both rhodium and gold were used for the electrode metal. However, other noble metals may be used.

The method according to the invention can be used to make humidity sensors which are small enough to include inside the housings of semiconductor devices, alongside the semiconductor device. When the resistance of the sensor is measured using A.C., no hydrogen (which harms semiconductor devices) is released, and the equilibrium between the moisture in the layer and the atmosphere in which the sensor is present will not be disturbed. The resistance of the sensor may alternatively be measured using D.C. when the presence of hydrogen can be tolerated. The sensors can be exposed to an ambient air atmosphere and can be resealed into a package without first needing to be recalibrated or dried for a long time.

During the investigations which led to the present invention, various compounds were prepared by reacting aluminum oxide gel with an orthophosphoric acid. The following compounds were found to be moisture-sensitive.

$Al_2O_3.P_2O_5$, having a trigonal crystal structure (berlinite)

$Al_2O_3.P_2O_5.3H_2O$ $Al_2O_3.P_2O_5.4H_2O$ (metavariscite)

$Al_2O_3.3P_2O_5$ $Al_2O_3.3P_2O_5.4H_2O$

It was not possible to determine the particular aluminium phosphate(s) present in the moisture-sensitive layers of humidity sensors made by the method according to the invention, since there was insufficient material in the moisture-sensitive layer to enable this determination to be carried out. It was found necessary to use thin, moisture-sensitive layers so that diffusion of moisture into or out of the layers would not be time-dependent.

A typical moisture-sensitive layer is formed by applying 8 mgm of 1 N orthophosphoric acid to a square alumina plate having 50 mm sides. The assembly is then heated to form the moisture-sensitive layer. The thickness of the moisture-sensitive layer (calculating the reaction products as $Al_2O_3.P_2O_5$) is about 60 nm. When layers were made which were thick enough to identify the particular form of the aluminium phosphate present in the layer, it was found that the rate of diffusion of moisture into and out of the layers was impracticably time-dependent.

Satisfactory humidity sensors have been made by a method according to the invention using 96% pure alumina, but it is preferred to use 99.5% pure alumina for the sake of stability of the devices after manufacture.

When phosphorus pentoxide is used to make the moisture-sensitive layer, it may be applied to the substrate by brushing, or by spinning or stencilling a suspension in an organic medium. Orthophosphoric acid may be applied, for example by brushing, spraying, stencilling or spinning.

Humidity sensors made by the method according to the invention may be used for testing the moisture content of the gaseous atmosphere inside the envelopes of devices such as acoustic surface wave devices or semiconductor devices, for example integrated circuits. This moisture content may increase, for example, from 50 p.p.m. immediately after sealing to 4400 p.p.m. 50 hours after sealing if the envelope and/or components have not been dried adequately. When the moisture contents of the atmospheres inside a set of devices have been measured at different times after sealing, it is possible to establish the drying procedures which are necessry in order to obtain the desired ultimate dryness of the gaseous atmospheres inside the devices. Such a humidity sensor may also be used to determine the moisture content, of the atmosphere inside an envelope containing a device, at which the electrical parameters of the device start to degrade. The sensitivities of humidity sensors made by the method according to the invention are not impaired when the moisture-sensitive layer is exposed to wet atmospheres, for example atmospheric air.

Two embodiments of the invention will now be described with reference to the Examples and the accompanying drawing.

DESCRIPTION OF THE PREFERRED EMBODIMENTS

EXAMPLE 1

Figure 1:
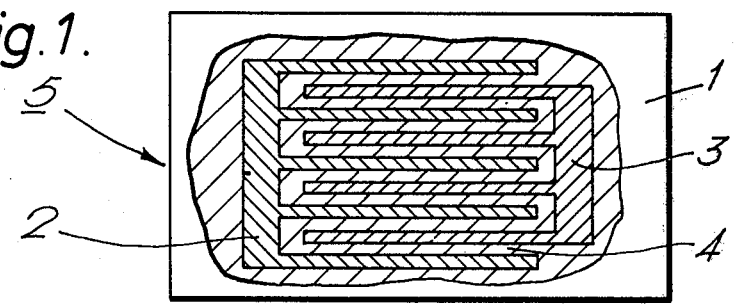
FIG. 1 is a plan view, partly in section, of a humidity sensor made by a method according to the invention.

An alumina substrate 1 (FIG. 1) consisted of 99.5% pure alumina and had dimensions of 2×1.5×0.5 mm. This substrate 1 was washed first with isopropanol and then with GENKLENE (Trade Mark) which is a grade of 1,1,1 trichloroethane marketed by I.C.I. Limited. A 1000 Å gold layer was sputtered onto the cleaned substrate 1 and an electrode system consisting of a pair of electrodes 2 and 3 was formed by making a photoresist mask (using Shipley AZ 1350 photoresist and AZ developer) and etching the gold using a conventional gold-etching solution consisting of a solution of iodine in ethanol.

After the etching had been completed, the residual photoresist was removed from the alumina substrate 1. The substrate 1 was then heated at 500° C. in air for 1 hour so as to remove any residual organic matter from the surface of the substrate 1 remaining between the electrodes 2 and 3 and to activate the substrate 1. A layer of 1 N orthophosphoric acid as then brushed onto the substrate 1 and the electrodes 2 and 3 in the vicinity of the electrodes. The assembly was then heated at 250° C. for 1 hour in nitrogen; at the end of this time the surface of the substrate 1 had a dry appearance, indicating that a moisture-sensitive layer 4 had been formed by a reaction between the alumina of the substrate 1 and the orthophosphoric acid. The assembly was then cooled.

Figure 2:
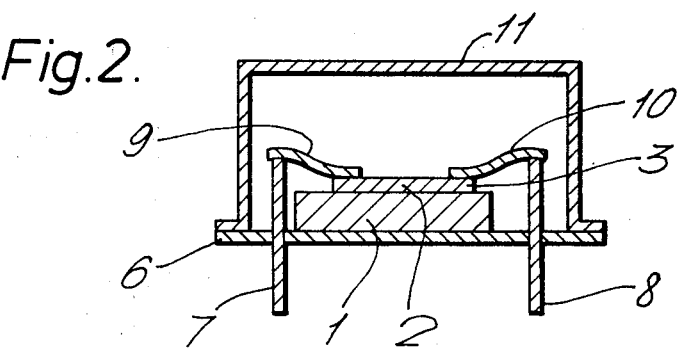
FIG. 2 is a cross-sectional view of a test cell comprising a housing containing a humidity sensor made by the method according to the invention.

A test cell shown in FIG. 2 was prepared using the above-described humidity sensor 5. The substrate 1 was secured mechanically (by means not shown) to a header 6 comprising lead-throughs 7 and 8. The lead-throughs 7 and 8 were electrically connected to the electrodes 2 and 3 by means of wires 9 and 10. A nickel housing 11 was welded to the header 6.

Figure 3:
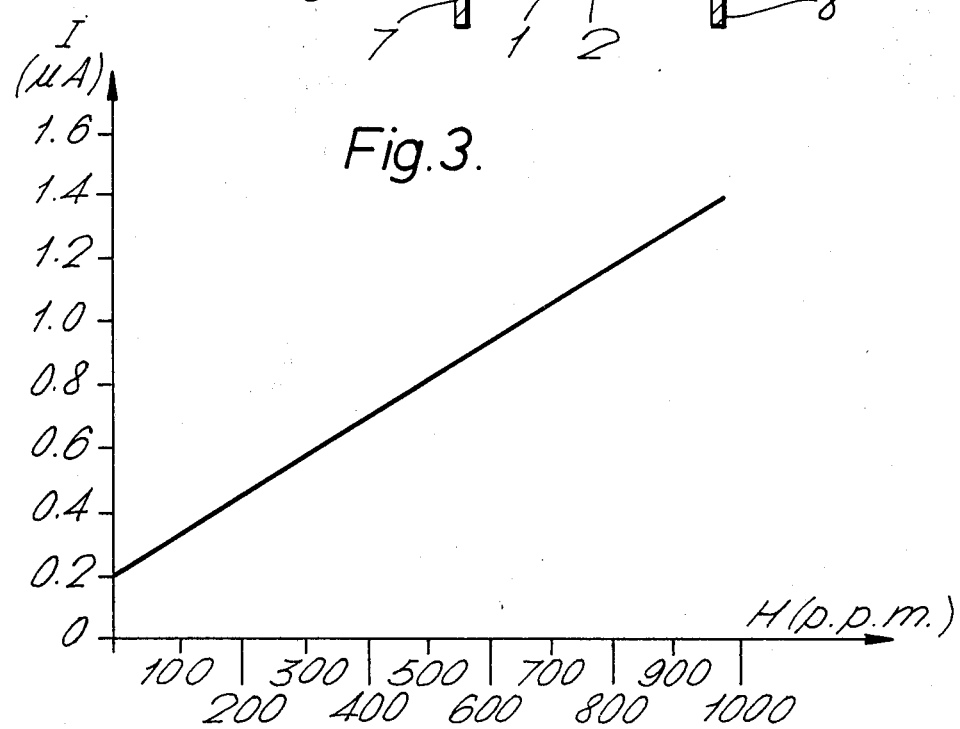
FIG. 3 is a graph showing the current-moisture characteristic of the humidity sensor described in Example 1.

FIG. 3 shows the A.C. current (I) versus the moisture (H) for this humidity sensor.

Figure 4:
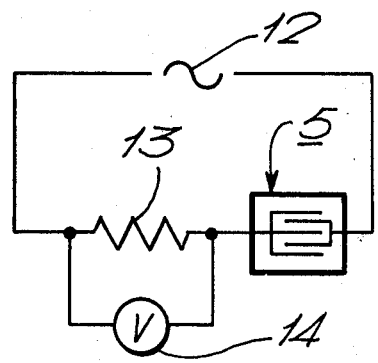
FIG. 4 is a schematic circuit diagram of a circuit used to calibrate the humidity sensor shown in FIG. 1.

FIG. 4 shows a circuit diagram of an arrangement used to calibrate the humidity sensor shown in FIG. 2. A source 12 supplies a 1 kHz A.C. peak-to-peak voltage of 10 volts through a 100 kΩ measuring resistor 13 which is connected in series with the humidity sensor 5. The voltage developed across the measuring resistor 13 is displayed on a Solartron 707S digital voltmeter 14.

By altering the concentrations of the orthophosphoric acid solution used, the processing temperatures and times, different current-moisture characteristics in the moisture content range from 3 to 15,000 p.p.m. may be obtained. Sodium fluoride, cesium fluoride, or ribidium fluoride are suitable for calibrating humidity sensors at the lower end of the range. These humidity sensors may be calibrated by means of a Faraday cell over a range from 2 to 10,000 p.p.m. $H_2O$, using a flowing gas stream to which controlled quantities of moisture are added.

If direct current measurement is used (for example using a D.C. voltage of 8 volts instead of the above-mentioned 10 volts 1 kHz A.C. voltage), the reading is taken within 30 seconds of applying a voltage across the resistive element so as to restrict the amount of hydrogen generated.

EXAMPLE 2

Figure 5:
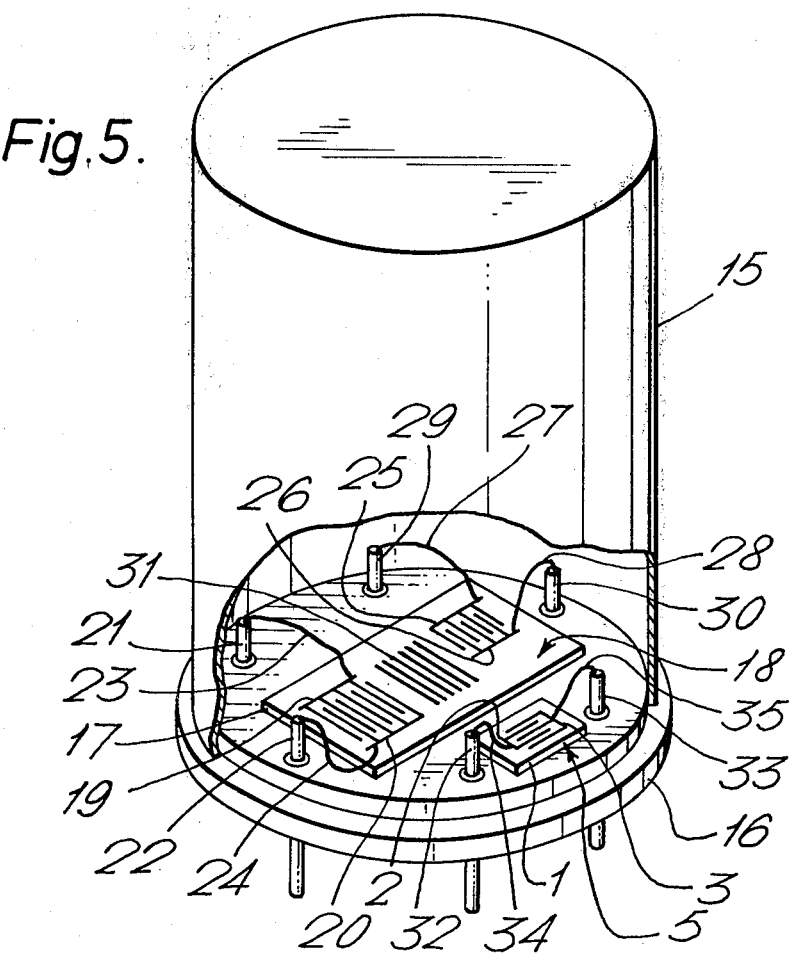
FIG. 5 is a perspective view, partly cut-away, of a surface acoustic wave device containing a humidity sensor made by the method according to the invention.

FIG. 5 shows a surface acoustic wave filter designed to filter electric signals. For the sake of clarity, part of the housing 15, which is made of nickel, is shown broken away. The filter comprises a piezoelectric wafer 17 which is bonded to a header 16 by means of an epoxy resin layer (not shown). The exposed main surface 18 of the wafer 17 bears a surface acoustic launching transducer array consisting of a first set of interdigitated electrodes 19 and 20. The electrodes 19 and 20 are connected to respective insulated lead-throughs 21 and 22 of the header 16 by respective lead wires 23 and 24. The main surface 18 carries a receiving transducer array spaced from the launching transducer array and consisting of a second set of interdigitated electrodes 25 and 26. The electrodes 25 and 26 are connected by leads 27 and 28 to insulated lead-throughs 29 and 30, respectively, of the header 16. Surface acoustic wave coupling means in the form of an array 31 of parallel conductive elements are located on the surface 18 between the launching transducer array 19 and 20 and the receiver transducer array 25 and 26.

A humidity sensor 5, similar to that described above with reference to FIG. 1, is incorporated in this filter by securing the alumina substrate 1 mechanically to the header 16 by means not shown. The electrodes 2 and 3 are electrically connected to insulated lead-throughs 32 and 33 of the header 16 by leads 34 and 35 respectively. The housing 15 is sealed to the header 16 by a conventional welding technique.

The humidity sensor 5 can be used to reduce the moisture content of the atmosphere within the housing 15 by passing a direct current through the moisture-sensitive layer, thereby electrolysing the moisture present in this layer and so converting the moisture into hydrogen and oxygen. By using the humidity sensor in this way, it would be practicable to significantly reduce the moisture content of the atmosphere in a sealed housing containing an electric circuit element such as a surface acoutic wave device provided that the hydrogen liberated does not have a deleterious affect on the performance of the electric circuit element.

I claim:

1. A method of making a humidity sensor comprising the steps of:
   providing an alumina substrate;
   providing a pair of noble metal electrodes on the substrate; and
   forming an electrically conductive, moisture-sensitive layer on the substrate between and electrically contacting the electrodes;
   characterized in that the moisture-sensitive layer is formed by:
   heating the alumina substrate to a temperature in the range of 100° to 750° C. for from 30 hours to ½ hour in order to activate the alumina;
   coating at least a portion of the substrate between the electrodes with orthophosphoric acid or phosphorus pentoxide, said coating contacting the electrodes; and
   heating the coated substrate to a temperature in the range of 50° to 500° C. for from 30 hours to ½ hour so as to form the electrically conductive, moisture-sensitive layer by a reaction between the alumina and the orthophosphoric acid or phosphorus pentoxide.

2. A method as claimed in claim 1, characterized in that the first heating step is performed in air, and it also removed any residual organic matter from the surface of the substrate.

3. A method of claimed in claim 2, characterized in that the coating step is performed with a ½ normal to 27 normal solution of orthophosphoric acid.

4. A humidity sensor made by the method of claim 1, 2, or 3.

* * * * *

UNITED STATES PATENT AND TRADEMARK OFFICE
CERTIFICATE OF CORRECTION

PATENT NO. : 4,343,688
DATED : August 10, 1982
INVENTOR(S) : MERVYN G. HARWOOD

It is certified that error appears in the above—identified patent and that said Letters Patent is hereby corrected as shown below:

Claim 2, Line 3, change "removed" to --removes--.

Claim 3, Line 1, change "of" to --as--.

Signed and Sealed this

Fourth Day of January 1983

[SEAL]

Attest:

*Attesting Officer*

GERALD J. MOSSINGHOFF
*Commissioner of Patents and Trademarks*